(12) United States Patent
Maccarrone et al.

(10) Patent No.: US 7,955,816 B2
(45) Date of Patent: Jun. 7, 2011

(54) DESIGN AND SYNTHESIS OF BIOTINYLATED PROBES FOR N-ACYL-ETHANOLAMINES

(75) Inventors: Mauro Maccarrone, Teramo (IT); Sergio Oddi, Teramo (IT); Filomena Fezza, Rome (IT); Alessandro Finazzi Agro', Rome (IT)

(73) Assignees: Universita Degli Studi Di Roma "Tor Vergata", Rome (IT); Universita Degli Studi Di Teramo, Teramo (IT)

( * ) Notice: Subject to any disclaimer, the term of this patent is extended or adjusted under 35 U.S.C. 154(b) by 133 days.

(21) Appl. No.: 12/299,249

(22) PCT Filed: May 2, 2006

(86) PCT No.: PCT/EP2006/061988
§ 371 (c)(1), (2), (4) Date: Dec. 11, 2008

(87) PCT Pub. No.: WO2007/128344
PCT Pub. Date: Nov. 15, 2007

(65) Prior Publication Data
US 2009/0118342 A1    May 7, 2009

(51) Int. Cl.
*C07D 235/00* (2006.01)
*C07D 333/78* (2006.01)
*C12Q 1/02* (2006.01)

(52) U.S. Cl. ............................. 435/29; 548/304; 549/33
(58) Field of Classification Search .................. 514/393; 435/29; 548/304.1
See application file for complete search history.

(56) References Cited

U.S. PATENT DOCUMENTS
6,358,682 B1    3/2002    Jaffee et al.

FOREIGN PATENT DOCUMENTS
WO    2005/085873    10/2005

OTHER PUBLICATIONS

McReynolds et al., Bioorganic & Medicinal Chemistry vol. 10 (2002), p. 625-637.*
Zhang et al. Bioorganic & Medicinal Chemistry, vol. 10 (2002), p. 2635-2639.*
Greg T. Hermanson, Bioconjugate Techniques, Chapters 13 and 14, (1997).*
K.D. McReynolds et al. "Non-natural glycosphingolipids and structurally simpler analogues bind HIV-1 recombinant gp120" Bioorganic & Medicinal Chemistry, vol. 10, No. 3, pp. 625-637 (2002).
Y. Zhang et al. "Detection of protein-ligand interaction on the membranes using C-terminus biotin-tagged alamethicin" Bioorganic & Medicinal Chemistry, vol. 10, No. 8, pp. 2635-2639 (2002).
Int'l Search Report for PCT/EP2006/061988, six pages (Aug. 7, 2007).
Written Opinion for PCT/EP2006/061988, eight pages (Aug. 7, 2007).

* cited by examiner

*Primary Examiner* — Yong Chu
(74) *Attorney, Agent, or Firm* — Nixon & Vanderhye P.C.

(57) ABSTRACT

The present invention relates to the synthesis and characterization of biotinylated analogue of N-arachidonoylethanolamine (AEA) and its use as a tool to study AEA transport and trafficking through biochemical and morphological techniques. In particular biotinylated AEA (b-AEA, for which we propose the common name MM22) is suitable to design highly sensitive and simple methods for the non-radioactive detection and quantitation of AEA from complex samples, which would offer a useful alternative approach to the routinely used radiometric assays. The invention also relates to the use of b-AEA as a potential therapeutic and diagnostic agent.

15 Claims, 7 Drawing Sheets

US 7,955,816 B2

DESIGN AND SYNTHESIS OF BIOTINYLATED PROBES FOR N-ACYL-ETHANOLAMINES

Figure 1A:
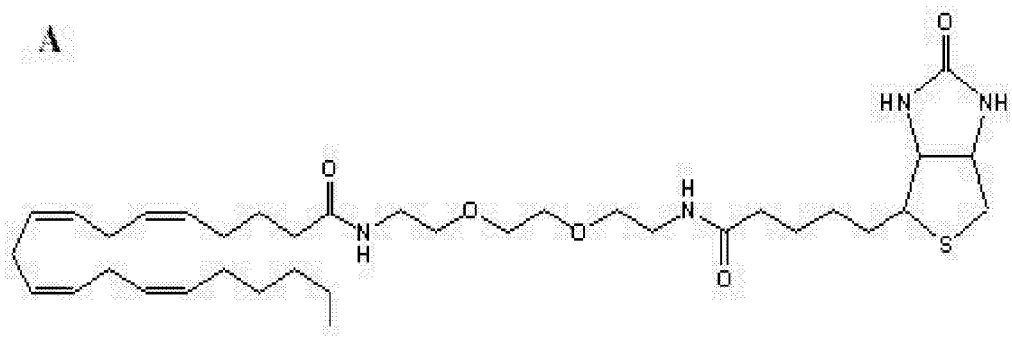

This application is the U.S. national phase of International Application No. PCT/EP2006/061988 filed 02 May 2006 which designated the U.S.; the entire contents of which are hereby incorporated by reference.

TECHNICAL FIELD OF THE INVENTION

The present invention relates to the synthesis and characterisation of biotinylated analogue of N-arachidonoylethanolamine (AEA) and its use as a tool to study AEA transport and trafficking through biochemical and morphological techniques. In particular biotinylated AEA (b-AEA, for which we propose the common name MM22) is suitable to design highly sensitive and simple methods for the non-radioactive detection and quantitation of AEA from complex samples, which would offer a useful alternative approach to the routinely used radiometric assays. The invention also relates to the use of b-AEA as a potential therapeutic and diagnostic agent.

BACKGROUND OF THE INVENTION

The endocannabinoid anandamide (N-arachidonoylethanolamine, AEA) activates type-1 (CB1R) and type-2 (CB2R) cannabinoid receptors [Howlett et al., 2004]. CB1R is localized mainly in the central nervous system, but is also expressed in peripheral tissues like immune cells. Conversely CB2R is predominantly expressed peripherally, but is also present in the brain. Therefore, activation of CB1 or CB2 receptors by AEA has many central and peripheral effects, that are terminated by cellular uptake through the AEA membrane transporter (AMT), followed by degradation to ethanolamine and arachidonic acid by the fatty acid amide hydrolase (FAAH) [Bari et al., 2006]. On the other hand, the checkpoint in AEA synthesis is the N-acyl-phosphatidylethanolamines (NAPE)-hydrolyzing phospholipase D (NAPE-PLD), which releases on demand AEA from membrane NAPEs [Fezza et al., 2005]. Together with AEA and other congeners like 2-arachidonoylglycerol, N-arachidonoyldopamine, noladin ether and virodhamine, the proteins that bind, transport, synthesize and hydrolyze these lipids form the "endocannabinoid system" [Bari et al., 2006]. Also the ability of AEA to bind to and activate type-1 vanilloid receptors (now called transient receptor potential channel vanilloid receptor subunit 1, TRPV1) has attracted growing interest, and in fact AEA is considered a true "endovanilloid". Interestingly, activation of CB1R or of TRPV1 by AEA can exert opposite biological effects, for instance by protecting or inducing, respectively, apoptosis in neuronal and peripheral cells [Bari et al., 2006].

A still unresolved, though critical, issue in endocannabinoid research is the mechanism by which AEA enters the plasma membrane and is transported inside the cells [recently reviewed by Battista et al., 2005]. The existence of a selective AEA membrane transporter (AMT) has been postulated. However, the molecular identity of AMT remains unknown, and, at present, molecular probes to test its expression at the protein or messenger RNA level are not yet available. In addition, the kinetic features of AEA uptake do not rule out other mechanisms of transmembrane transport, being compatible, for example, with a simple diffusion process driven by FAAH-catalyzed hydrolysis of AEA. However pharmacological, biochemical and confocal microscopy studies strongly suggest that an authentic AEA membrane transporter exists, and that this is distinct from FAAH [Oddi et al., 2005].

The lack of cloning and expression of the transporter protein has prevented the development of molecular tools like oligonucleotides or antibodies, able to give definitive proof of the presence on the cell surface of an active membrane transporter for AEA (AMT) for AA or other equivalent fatty acids.

A recent report has identified a high-affinity binding site involved in the transport of endocannabinoids, by means of a potent, radiolabelled competitive inhibitor of AEA uptake: LY2318912 [Moore et al., 2005].

However, to date only one non-radioactive AEA analogue able to visualize AEA movement inside the cells by mean of fluorescence microscopy has been described [Muthian et al., 2000]. This compound, named SKM 4-45-1, is nonfluorescent until it is transported into the cells, where cytosolic esterases can activate its fluorescein moiety.

The mechanisms responsible for the AEA uptake and transport are not yet well characterized, primarily because of the lack of suitable molecular tools. In fact, although the current radiometric-based techniques using radiolabeled compounds such as [$^{3}$H]AEA, [$^{14}$C]AEA or [$^{125}$I]LY2318912 yield a great sensitivity for the analysis of the kinetic features of AEA transport, they do not allow to visualize its specific pathways for internalization and intracellular targeting. Moreover, radioisotopes and radioimmunoassays used for these purposes, are not only very expensive, but arise problems due to the hazard of working with, and disposing of, radioactive materials.

On the other hand, SKM 4-45-1 is nonfluorescent in the extracellular environment and becomes fluorescent only when exposed to intracellular esterases. Therefore, its use is restricted to intracellular compartments of cells that express a sufficient esterase activity [Muthian et al., 2000], and is not suitable to visualize AMT on the cell surface [Oddi et al., 2005]. Another limitation of SKM 4-45-1 is that the manifestation of intracellular fluorescence occurs as a result of two kinetic processes, uptake and intracellular de-esterification. Therefore, the utility of SKM 4-45-1 in kinetic studies of AEA transport is extremely limited.

Furthermore, due to low signal intensity associated with direct fluorescence, SKM 4-45-1 does not prove of particular efficacy for the fine morphological analyses of the intracellular trafficking and metabolism of AEA [Muthian et al., 2000].

In order to shed some light on the metabolic regulation of AEA and related fatty acid amides activity, it would be very useful to avail means capable of visualizing through microscopy techniques the transport and intracellular trafficking of these lipids within cells and tissues.

Hence, a first scope of the present invention was to provide means suitable to trace AEA transport and trafficking by biochemical and morphological techniques.

Clinical/Diagnostic Relevance of Cannabinoid System

The impressive expansion of cannabinoid research in the past decade provided a large body of data regarding the potential involvement of endocannabinoid system in an ever-increasing number of pathological conditions, including neurological, cardiovascular, gastrointestinal, reproductive disorders, and cancer [Bari et al., 2006]. Therefore, alteration of the activity of one component of this system, such as the AEA membrane transporter, could have therapeutic value for the treatment of several human diseases.

Among endocannabinoids, anandamide (AEA) signaling has been involved in a number of physio-pathological conditions and has been attracted growing interest in pharmacology for its multiple diagnostic and/or therapeutic use, for example, in several disorders of central nervous system (CNS), in inflammatory conditions, pregnancy failure, pain treatment, and anxiety management [Bari et al., 2006]. Physiological experiments show, in fact, that AEA may be as important in regulating our brain functions in health and disease as other better-understood neurotransmitters, such as dopamine and serotonin. In particular, endogenous levels of AEA are elevated in the cerebrospinal fluid of Parkinson's disease and schizophrenic patients [Pisani et al., 2005]. In the latter subjects, AEA was supposed to be released in response to psychotic symptoms, in order to help their control, rather than to trigger psychosis. Furthermore, in a murine model of multiple sclerosis, the AEA content is altered in brain region involved in the disease and inhibition of endocannabinoid uptake significantly ameliorated spasticity. In this line, a recent article clearly demonstrates that cannabinoid type 1 receptors (CB1R) play an important role in neuroprotection by endogenous cannabinoids. Administration of kainic acid (KA), an excitotoxin that induces neuronal seizures in vivo, rapidly increased hippocampal levels of AEA that induced protection against excitotoxicity [Bari et al., 2006].

In addition, several reports have shown that the activation of the central endocannabinoid system increases food intake and promotes weight gain. In genetic animal models of obesity, brain endocannabinoid levels are increased and CB1R is downregulated. Recently, an increase of circulating endocannabinoids levels has been reported in obese women. In this line Rimonabant (SR141716), a selective antagonist of CB1R developed by Sanofi-Aventis, has also been developed as an anti-obesity drug [Bari et al., 2006].

In peripheral systems, the detection of high levels of AEA in the uterus has been reported to indicate a high chance of miscarriage, which seems of great diagnostic interest and has screening potential. The important role of screening and quantifying AEA as a risk factor for cardiovascular disease and vascular dysfunction was also emphasized by other reports [Bari et al., 2006].

Therefore a simple, sensitive and cheap method to measure the concentration of AEA in biological fluids and tissues would be very useful and of diagnostic value. Its development could be possible by using b-AEA (MM22).

With respect to the potential therapeutic value of AEA, it has been found that administration of AEA provides relief in several models of neuropathic and inflammatory pain. Unfortunately, this compound is rapidly inactivated by enzymatic hydrolysis, which prevents its effective medical use. On the other hand, more metabolically stable agonists of cannabinoid receptors present unwanted psychotropic side effects, including memory impairment and catalepsy. It seems of interest that, as demonstrated in this invention, b-AEA is not hydrolyzed by FAAH and does not bind to CB or TRPV1 receptors.

Therefore, a further purpose of the invention was to provide a means to prolong the physiological effects of AEA, by controlling its uptake and the hydrolysis.

SUMMARY OF THE INVENTION

During the research program for novel analytical tools for studying the active transport of N-acyl-ethanolamines through the cellular membrane, it has been discovered that biotinylated derivative of N-acyl-ethanolamines, such as N-arachidonoylethanolamine (AEA) or its fatty-acid analogues, exhibit unexpected properties that make these biotinylated compounds useful agents in analytical, diagnostic and therapeutic methods.

In fact, first of all, the biotinyl derivatives, which are suitable to link a marker capable of being detected, do not interfere with the active transport machinery through the cellular membrane. Biotinylated AEA, as an example of biotinyl derivative, competes with the circulating AEA for the AMT system and is efficiently transported within the cell.

A second property is that the biotinyl-derivatives are not hydrolyzed by the endo-cellular hydrolase system. In particular the b-AEA is actively transported within the cell by the AMT system, however, without subsequently being hydrolyzed by the FAAH enzyme and without interfering with CB1 receptor. As a result, b-AEA accumulates within the cell with a concentration-dependent kinetics, and causes the active transport of circulating AEA to be reduced with an $IC_{50}$ of $0.5\pm0.1$ $\mu M$. The inhibited transport of AEA within the cell delays its hydrolysis and accordingly prolongs its physiological activity.

Practically, the biotinyl-fatty acid-ethanolamine compounds described here are useful analytical means for studying the active machinery involved in the internalization of these nervous system as well as peripheral mediators. For example, biotinyl-AEA (b-AEA, identified as MM22) seems to be a unique tool for the visualization of AMT by fluorescent microscopy techniques, which is safer, cheaper and easier to use than radiographic methods. In particular, the widespread use of biotin as a "tag", easily and efficiently recognized by secondary detection reagents in several applications, warrants the wide validity of b-AEA for imaging, as well as measurement, of AEA transport in many cell types and tissues. In addition, the stability of b-AEA, that is not hydrolyzed by FAAH, makes it suitable also to follow the fate of AEA within the cell, and its trafficking among cell compartments.

Moreover, due to its properties b-AEA is useful as a diagnostic agent and as a modulator of the cannabinoid system, thus in the diagnosis and treatment of all those pathological pictures which are characterized by impairment of the cannabinoid system and which can be alleviated by the inhibition of the AEA cellular uptake and by the maintenance of its high extracellular concentration.

Accordingly, a first object of the present invention is a biotinyl-N-acyl-ethanolamine compound having formula I, wherein $R_1$ is a spacer arm and $R_2$ is a saturated or unsaturated fatty acid residue.

A second object of the invention is a process for the preparation of the biotinyl-N-acyl-ethanolamine derivatives of the invention comprising the step of reacting an active form of a saturated or unsaturated fatty acid with a biotinylating reagent at suitable operation conditions, optionally purifying the obtained biotinyl fatty acid.

A third object of the invention is a reagent comprising a biotinyl-N-acyl-ethanolamine according to the invention as an analytical probe for visualizing the internalization and trafficking of N-acyl-ethanolamine in intact cells, as a tool for isolating, studying and monitoring the transporter molecules, as an affinity partner for affinity chromatography or magnetic isolation devices, as a component of competitive assays for detecting N-acyl-ethanolamine in solution-based systems, as a cell marker for flow cytometry application. Preferably, object of the invention is the biotinyl-AEA as a tool for visualizing the internalization and trafficking in the cell of AEA, for isolating and studying the AEA transporter molecules, as a cell marker for flow cytometry application and identification of AMT-expressing cells.

A further object of the invention is a diagnostic agent comprising a biotinyl-N-acyl-ethanolamine, such as biotinyl-AEA for monitoring parameters of the endocannabinoid system and as diagnostic reagent for the diagnosis of disorders of the central nervous system, inflammation conditions, risk for pregnancy failure, risk for cardiovascular diseases and vascular dysfunctions, multiple sclerosis, tendency to obesity.

Still further objects of the invention are kits of reagents for use in analytical and diagnostic methods, comprising a biotinyl-N-acyl-ethanolamine of the invention and a biotin-affinity ligand capable of being detected, this ligand being labeled with a detectable moiety selected from the group comprising: fluorophores, fluorescent microspheres, enzymes, chromophores, magnetic particles or colloidal gold.

A still further object of the invention are biotinyl-N-acyl-ethanolamines, such as biotinyl-AEA, as medicaments, and compositions comprising the same, for the inhibition of N-acyl-ethanolamine uptake within the cells, in particular for use in the treatment of neuropathic and inflammatory pain, anxiety, disorders of central nervous system, inflammatory conditions, neurological, cardiovascular, gastrointestinal, reproductive disorders, anxiety, cancer and multiple sclerosis, and as a vector for carrying substances within the viable cells.

Other objects will be evident in view of the following detailed description.

Since b-AEA shares several of the unique advantageous features of the recently developed AEA uptake inhibitors, i.e. inhibition of AMT, but not of FAAH, inactivity at cannabinoid/vanilloid receptors and metabolic stability, apart from its utility for the visualization of AEA transport and trafficking, it is likely that b-AEA can be used also as a novel specific AEA uptake inhibitor.

SHORT DESCRIPTION OF THE FIGURES

Figure 1B:
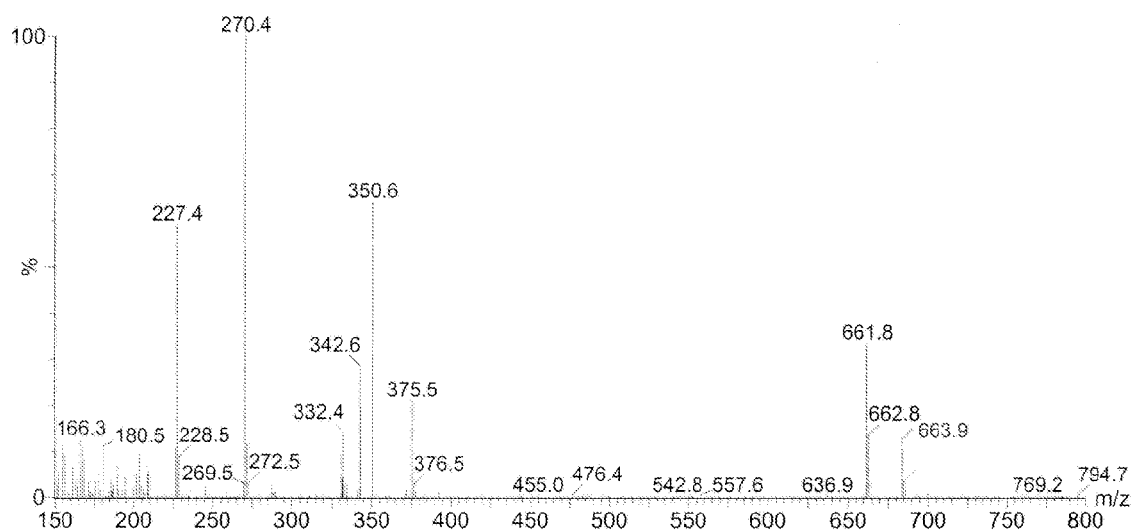
Figure 1C:
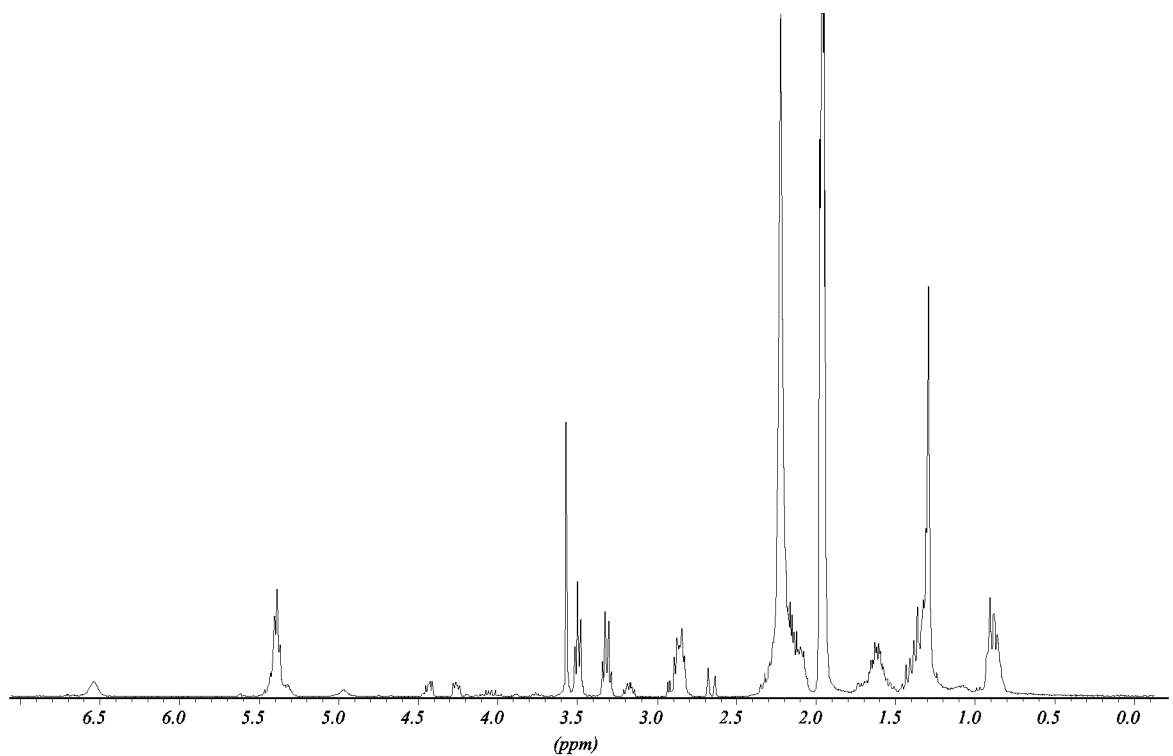

FIG. 1: Characteristics of biotin-AEA (b-AEA)
Panel (A) reports the chemical structure of b-AEA; panel (B) illustrates the MS spectrum of b-AEA and panel (C) illustrates the $^1$H-NMR spectrum of b-AEA.

FIG. 2: The flowcharts represent the metabolism and binding of AEA or biotin-AEA (b-AEA) in keratinocytes (HaCaT cells). Panel A) illustrates the dependence of the AEA membrane transporter (AMT) on substrate concentration. Panel B) illustrates the substrate dependence of fatty acid amide hydrolase (FAAH) activity. Panel C) illustrates the binding curves of [$^3$H]AEA and [$^3$H]b-AEA to CB1 receptors. Data are means±S.D. of three independent experiments.

Figure 3:
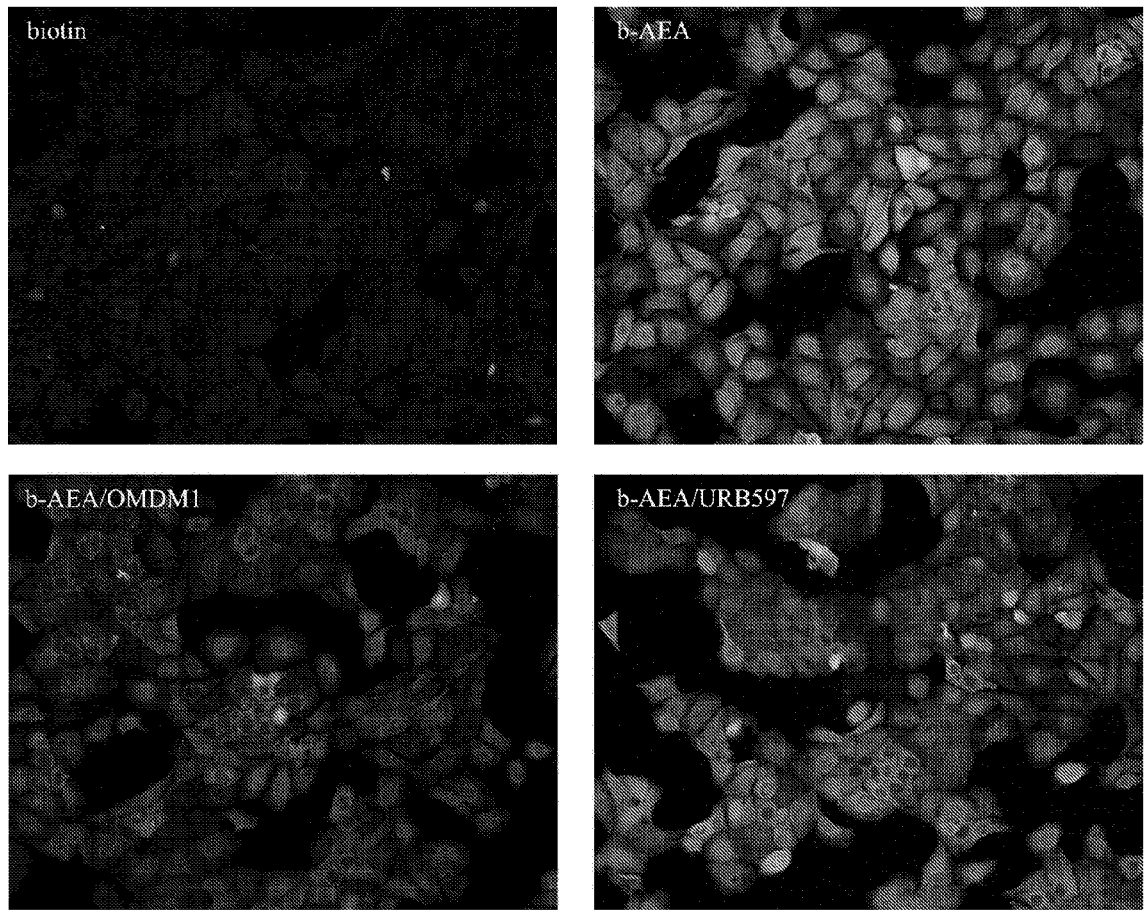

FIG. 3: Reports the results of the fluorescence microscopy studies of the metabolism of biotin-AEA (b-AEA) in human HaCaT cells.

Cells were pretreated with or without the indicated compounds, and then were incubated with EZ-Link Biotin-PEO-Amine, as negative control, or b-AEA for 5 min. After fixation, cells were immunostained and observed under the fluorescence microscopy. No green fluorescence could be detected in negative controls, demonstrating that EZ-Link Biotin-PEO-Amine was not able per se to cross the plasma membrane (biotin). Instead, biotin-AEA (b-AEA) was internalized, and this process was minimized by the AMT inhibitor OMDM-1 (b-AEA/OMDM1), but not by the FAAH inhibitor URB597 (b-AEA/URB597). Images are representative of at least three independent experiments, and five fields were examined for each treatment.

Figure 4:
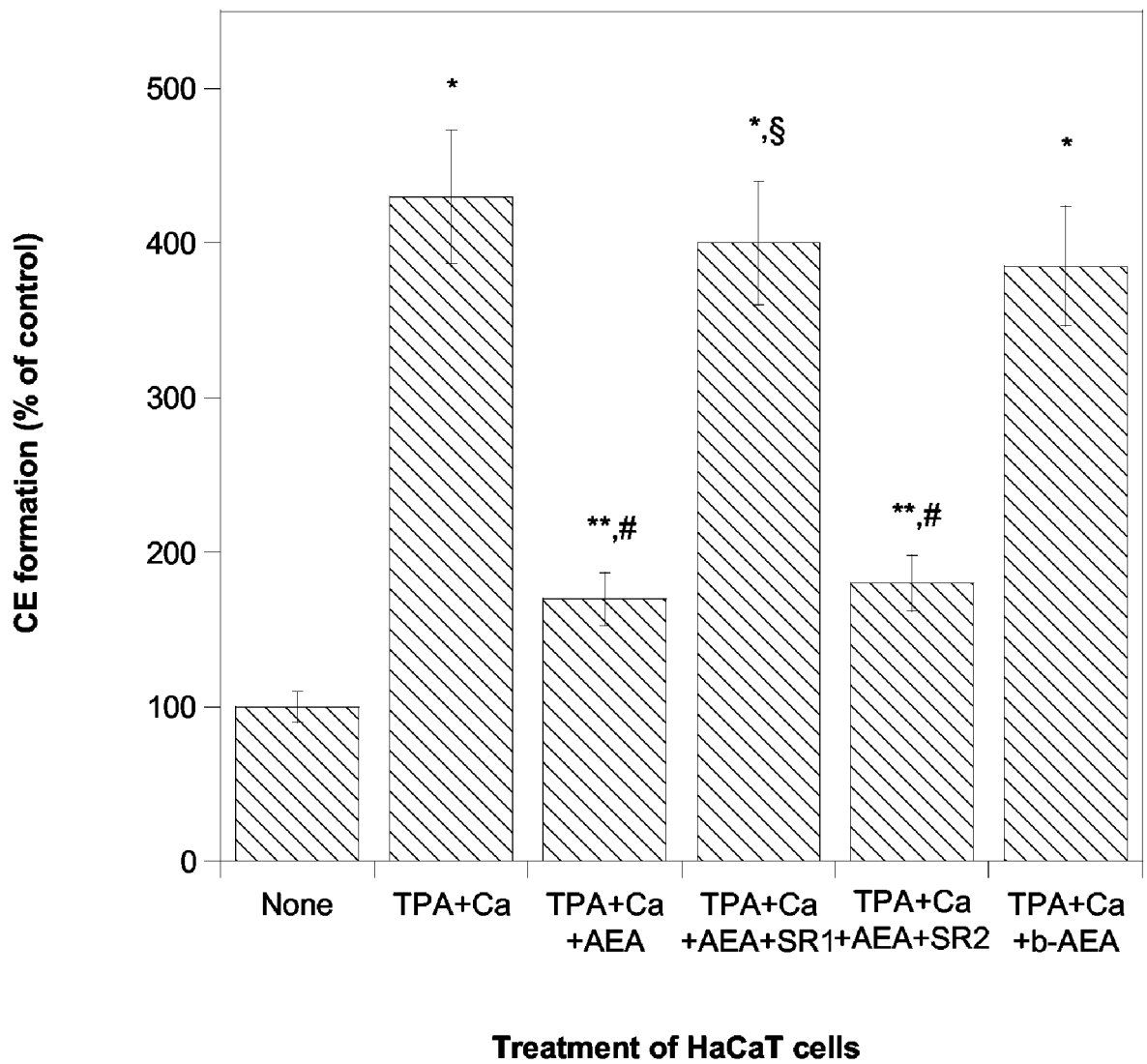

FIG. 4: Effect of AEA and biotin-AEA (b-AEA) on HaCaT cell differentiation.

The effect of AEA or b-AEA, each used at 1 M alone or in the presence of 0.1 μM SR141716 (SR1) or 0.1 μM SR144528 (SR2), was tested on cornified envelope (CE) formation induced in HaCaT cells by treatment with TPA+calcium (Ca) for 5 days (100%=0.075±0.007 $A_{600}$ units per mg protein). Data are means±S.D. of three independent experiments. * Denotes p<0.01, and ** denotes p<0.05 versus controls; # denotes p<0.05 and @ denotes p<0.01 versus TPA+Ca; § denotes p<0.01 versus TPA+Ca plus AEA (p>0.05 in all other cases).

DETAILED DESCRIPTION OF THE INVENTION

Compounds
The new compounds of the invention are molecules having the following general formula I:

Formula I

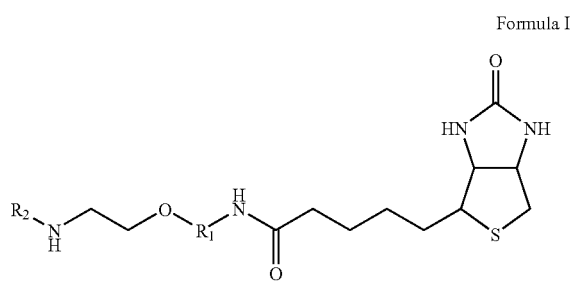

where the spacer arm ($R_1$) can be:

| spacer arm | |
|---|---|
| $R_{1A}$ | 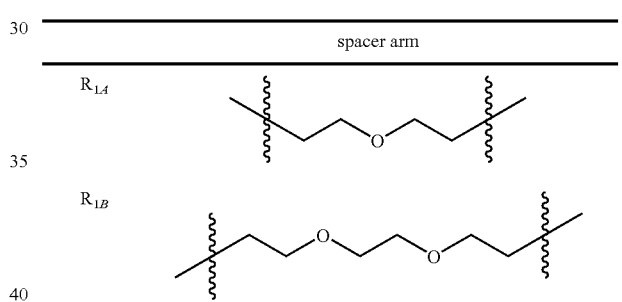 |
| $R_{1B}$ | | and the fatty acid ($R_2$) can be any saturated or insaturated fatty acid such as arachidonic acid, palmitic acid, oleic acid, stearic acid and alpha-linolenic acid, as illustrated below.

| Fatty acid |
|---|
| Arachidonic acid |
| Palmitic acid |
| Oleic acid |

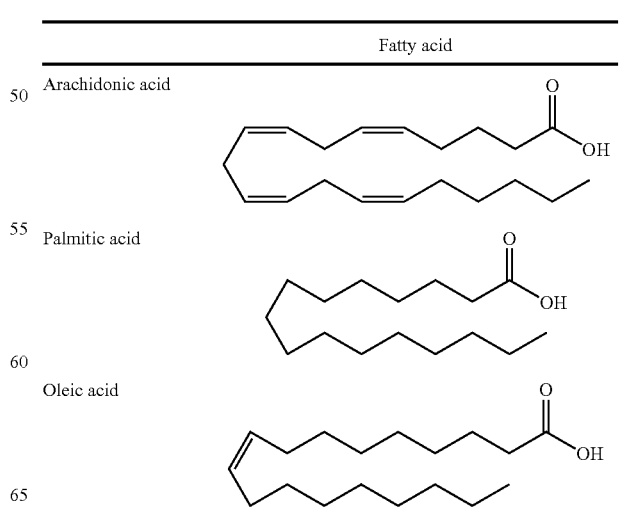

-continued

Fatty acid

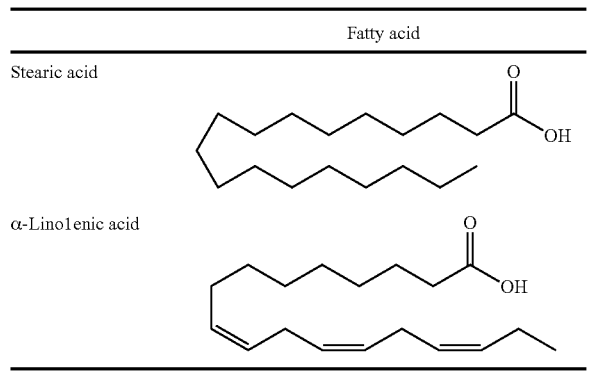

Stearic acid

α-Linolenic acid

Method of Preparation

The biotin-derivatives of N-acyl-ethanolamines of formula I are prepared using biotinylating reagents well-known to the skilled person and commercially available. The reagents comprise the biotinyl moiety directly linked to a functional group capable of reacting to the compound to be labeled or, preferably, spaced through a spacer arm comprising oxygen atoms and alkyl groups. For instance, biotinylating reagents commercialized under the Trade Mark EZ-Link Biotin-PEO-Amine or EZ-Link Biotin-LC-PEO-Amine (Pierce) may be advantageously employed for the preparation of the compounds of the invention.

The compounds of the invention are prepared following a general method of chemical synthesis. A solution comprising the saturated or unsaturated fatty acid, the compound O-(7-azabenzotriazol-1-yl)-N,N,N',N'-tetramethyluronium-hexafluorophosphate or in alternative O-benzotriazol-1-yl-N,N,N',N'-tetramethyluronium tetrafluoroborate (TBTU) as carboxylic acid activating agent, and N,N-diisopropylethylamine (DIPEA) or equivalent tertiary amine (i.e. triethylamine) is prepared using an organic anhydrous aprotic solvent. Suitable solvents are dimethylformamide (DMF), dichloromethane ($CH_2Cl_2$) and tetrahydrofurane (THF). After stirring for 0,5 to 1,5 hours, a biotinylation reagent is added to the solution and the resulting mixture is stirred, preferably at room temperature for 15 to 30 hours, for instance for 24 h.

The obtained biotinyl compound can then be isolated and purified according to any suitable well-known procedure. For instance, the reaction solution may be diluted with organic solvent such as ethyl acetate, acetone, chloroform, ethanol or any other alcohol and water. The organic phase is washed sequentially with an acid solution, and with a buffer solution. Finally the synthesized compound is recovered from the organic phase, for instance by drying, or concentrated under reduced pressure and purified by chromatography, for example on silica gel (0-15% methanol in chloroform), to obtain the biotin-derivative. The biotinylated compound is recovered with yields ranging from 38 and 55%.

By following the same method, under the same experimental conditions, it is possible to synthesize the corresponding radioactive biotin-compounds, which are necessary for carrying out the experimental work. In these cases a mix of fatty acid and the corresponding [$^3$H]-fatty acid (specific activity 10 mCi/mmol) can be used.

The reactions for the preparation of the biotinyl compounds of the invention can be easily monitored by thin-layer-chromatography (TLC) or any other analytical technique, and the final compounds are characterized by high performance liquid chromatography-electron spray ionization-mass spectrometry (HPLC-ESI-MS) and $^1$H nuclear magnetic resonance ($^1$H NMR). By way of example, FIG. 1 reports the chemical structure (A), the ESI-MS spectrum (B) and $^1$H NMR spectrum (C) of b-AEA.

Applications

Analytical Reagent:

The biotinylation provides a "tag" that labels and transforms a poorly detectable compound such as AEA into a probe (biotinyl-AEA, b-AEA or MM22) easily and efficiently detectable with indirect immunofluorescence. This probe is selectively taken up by the cells via the same AMT-mediated mechanism that transports AEA, as it is inhibited by a specific inhibitor of AMT. In fact, we found that b-AEA is specific for AMT, and does not interact with the other endocannabinoid system components, such as CB1R, CB2R, TRPV1 or FAAH, at least within low micromolar concentrations. For this reason the biotinylated fatty acid ethanolamides of the invention are useful tools, first of all, for characterizing and isolating the cell membrane transporter system or transporter molecules by morphological and functional assays, and secondly for studying and monitoring the intracellular trafficking and metabolism of these compounds acid within the cells.

The tagged molecule can then be detected with an appropriate affinity partner, such as avidin or anti-biotin antibodies, that have been labeled with a molecule capable of being detected. Suitable detectable molecules are fluorophores, fluorescent microspheres, enzymes, chromophores, magnetic particles or colloidal golds, allowing to explore the transport mechanism with stains compatible for light, electron and fluorescence microscopy.

The biotinyl N-acyl-ethanolamines of the invention and the biotin-affinity partner capable of being detected can also be assembled in a kit of parts suitable for coordinated use in an analytical or diagnostic method.

As to b-AEA, apart from its application as a probe to visualize by microscopy techniques the AEA transport, there are several other applications.

Namely, b-AEA can be used as a "bait" to specifically bind its target molecules in a cell lysate (or any other molecular suspension). As a biotinylated probe, b-AEA and its interacting molecules can be isolated by means of an avidin-based affinity system, including chromatography or magnetic isolation devices.

Moreover, b-AEA may be also useful to label cells for flow cytometry applications. For example, b-AEA is suitable for labeling cells highly expressing AMT, and to count (and eventually separate) them from a heterogeneous population by magnetic or fluorescence-activated cell flow sorting.

Finally, b-AEA probing and recognition system (based on avidin- or anti-biotin approaches) is also compatible with solution-based methods such as enzyme-linked immunosorbent assays (ELISAs). For example, the AEA present in a solution could be quantified by means of a competitive assay, based on the competitive binding of AEA and b-AEA to the bovine serum albumin.

Diagnostic Reagent:

The peculiar properties of biotinyl compounds of the invention make these compounds useful as diagnostic reagents for monitoring the level of circulating AEA, and its saturated or unsaturated fatty acid analogues, and for recognizing any unpaired parameter in the endocannabinoid system. In fact, altered levels of endogenous AEA are characteristic of many pathological states. Elevated levels of AEA are observed in the cerebrospinal fluid of Parkinson's disease as well as schizophrenic patients. In the latter subjects, AEA was supposed to be released in response to psychotic symptoms, in order to help their control, rather than to trigger psychosis.

Furthermore, in a murine model of multiple sclerosis, the AEA content is altered in brain region involved in this disease. Moreover, in genetic animal models of obesity, brain endocannabinoid levels are increased and CB1R is down-regulated. In fact, recently an increase of circulating endocannabinoids levels has been reported in obese women. In peripheral systems, the detection of high levels of AEA in the uterus has been correlated to a high chance of miscarriage, which seems of great diagnostic interest and has broad screening potential. Finally, it has been reported in literature that AEA level is an important factor to quantify the risk for cardiovascular disease and vascular dysfunction.

Therefore, biotinyl-AEA is a very useful agent to develop a simple, sensitive and cheap method to measure the concentration of AEA in biological fluids and tissues, and as such it has a remarkable diagnostic value. Suitable diagnostic assays are competition assays in homogeneous or heterogeneous phase, such as for example enzyme-linked immunosorbent assays (ELISAs), fluorescence-assays and capillary electrophoresis systems.

Therapeutic Applications

There exists in literature a large body of data regarding the involvement of endocannabinoid system in an ever-increasing number of pathological conditions, including disorders of central nervous system, inflammatory conditions, neurological, cardiovascular, gastrointestinal, reproductive disorders, anxiety, cancer and multiple sclerosis. Therefore, alteration of the level and/or activity of one component of this system, such as AEA or AEA membrane transporter, has therapeutic value for the treatment of several human diseases.

Since biotinyl-AEA shares several of the unique advantageous features of the recently developed AEA uptake inhibitors, i.e. competitive inhibition of AMT, but not of FAAH, inactivity at cannabinoid/vanilloid receptors and metabolic stability, b-AEA and its congeners are suitable as novel specific AEA uptake inhibitors. By inhibiting the transport of endogenous circulating AEA across the cell membrane, b-AEA actually reduces the degradation of AEA and accordingly potentiates its effect.

Along this line, it has been observed that in a murine model of multiple sclerosis the AEA content is altered in brain region involved in this disease, and inhibition of endocannabinoid uptake significantly ameliorates spasticity.

Other therapeutic applications of b-AEA are in the context of analgesia, specifically in providing relief against neuropathic and inflammatory pain, and in the treatment of anxiety.

Experimental Work

Metabolism of b-AEA

Figure 2A:
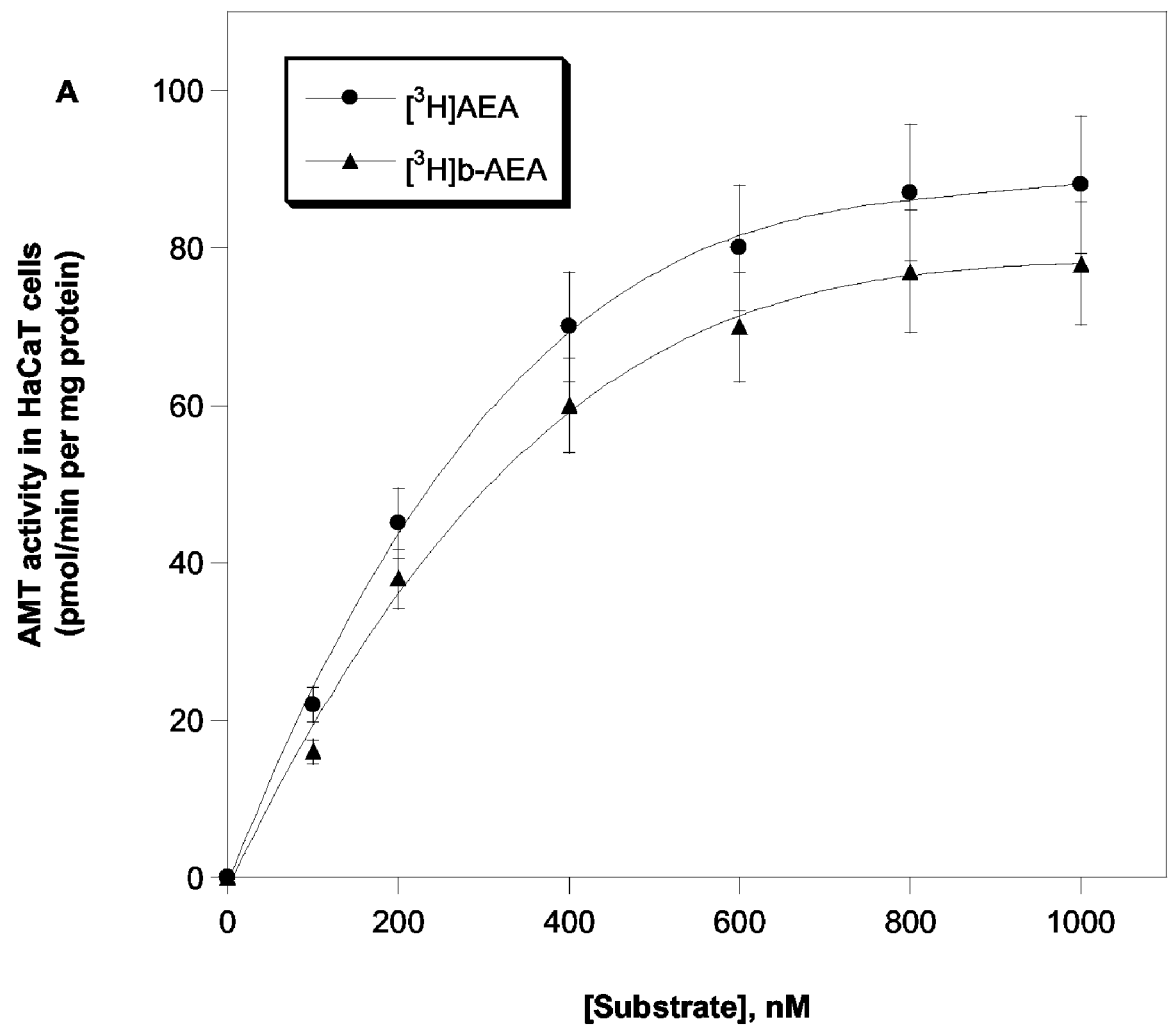

The ability of [$^3$H]b-AEA to across the membrane was tested in intact HaCaT cells, that were able to accumulate [$^3$H]b-AEA in a concentration-dependent manner typical of a saturable process (FIG. 2A). Accumulation of [$^3$H]b-AEA was similar to that of [$^3$H]AEA (FIG. 2A), and showed apparent Km and Vmax values of 421±88 nM and 116 ±10 pmol/min per mg protein, respectively (Table 1). These kinetic constants are typical of AMT in HaCaT cells.

Figure 2B:
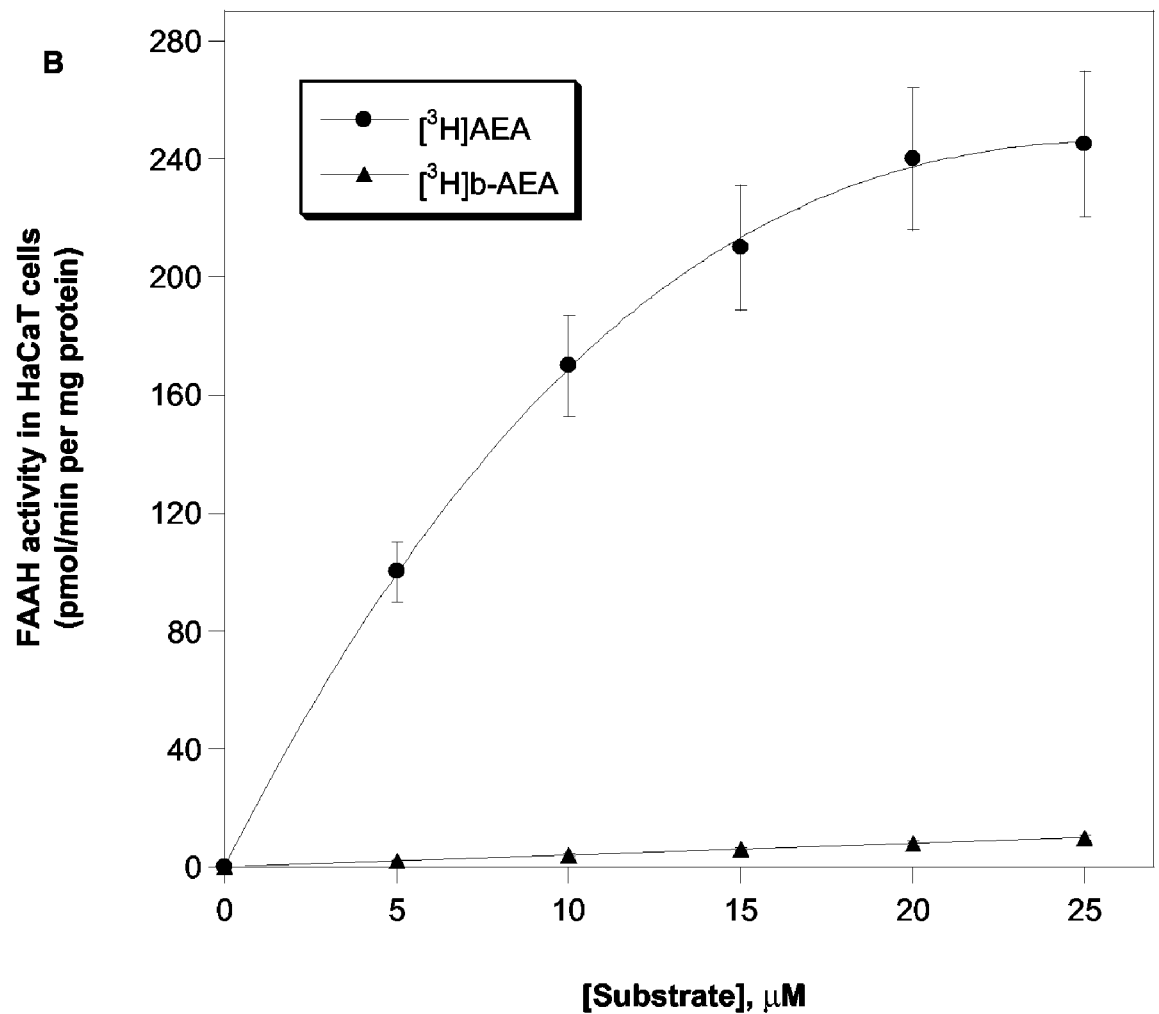

Unlike [$^3$H]AEA, that was hydrolyzed in a concentration-dependent manner (FIG. 2B) and with kinetic constants (Table 1) typical of FAAH in HaCaT cells, [$^3$H]b-AEA was not a substrate for FAAH (FIG. 2B). In addition, [$^3$H]b-AEA did not bind to CB1 receptors of HaCaT cells (FIG. 2C), at variance with [$^3$H]AEA that bound to these receptors (FIG. 2C) with apparent Kd and Bmax values (Table 1) close to those already found in HaCaT cells [Maccarrone et al., 2003].

To further characterize the biochemical profile of biotin-AEA, an inhibition assay was performed, where the effect of this "cold" AEA derivative was evaluated on the transport, hydrolysis and biosynthesis of [$^3$H]AEA. The results, shown in Table 2, demonstrate that b-AEA does not affect FAAH activity nor NAPE-PLD activity of HaCaT cells at concentrations up to 10 µM, while it does reduce AEA uptake by AMT with an IC$_{50}$ value of 0.5±0.1 µM. The latter IC$_{50}$ value, showing that 0.5 µM b-AEA reduced by half the uptake of 0.5 µM [$^3$H]AEA, further corroborates the observation that AMT has similar affinity towards AEA and its biotinylated derivative (see Km values of AMT in Table 1).

Moreover, the ability of b-AEA to inhibit the binding of the synthetic cannabinoid [$^3$H]CP55.940 to authentic CB1 or CB2 receptors was tested. To this end, membrane preparations from mouse brain or mouse spleen were used, as sources of authentic CB1R or CB2R respectively. In the same line, the ability of b-AEA to bind to TRPV1 was investigated, performing competition assays with the specific receptor agonist [$^3$H]RTX. The results, summarized in Table 2, show that b-AEA was inactive on CB1, CB2 or TRPV1 receptors, having IC$_{50}$ values>10 µM in all cases. Taken together, the biochemical data suggest that b-AEA is transported by AMT with the same efficacy as AEA, but is not a substrate for FAAH, does not interfere with NAPE-PLD, and does not bind to the AEA-binding receptors CB1R, CB2R or TRPV1.

TABLE 1

Kinetic constants of AMT, FAAH or CB1R in HaCaT cells, using AEA or biotin-AEA (b-AEA) as substrate or ligand.

| Parameter | Kinetic constant | |
|---|---|---|
| AMT | Km (nM) | Vmax (pmol/min per mg protein) |
| AEA | 353 ± 60 | 124 ± 8 |
| b-AEA | 421 ± 88 | 116 ± 10 |
| FAAH | Km (M) | Vmax (pmol/min per mg protein) |
| AEA | 13 ± 2 | 385 ± 25 |
| b-AEA | — | — |
| CB1R | Kd (nM) | Bmax (fmol per mg protein) |
| AEA | 173 ± 38 | 926 ± 63 |
| b-AEA | — | — |

TABLE 2

IC$_{50}$ values of biotin-AEA (b-AEA) on the transport, hydrolysis and biosynthesis of AEA, and on CB1R, CB2R and TRPV1 binding.

| Parameter | IC$_{50}$ (M) |
|---|---|
| AMT[a] | 0.5 ± 0.1 |
| FAAH[b] | >10 |
| NAPE-PLD[c] | >10 |
| CB1R[d] | >10 |
| CB2R[e] | >10 |
| TRPV1[f] | >10 |

[a]Activity was measured in intact HaCaT cells with 500 nM [$^3$H]AEA as substrate (control = 80 ± 9 pmol/min per mg protein).
[b]Activity was measured in HaCaT cell extracts with 10 µM [$^3$H]AEA as substrate (control = 170 ± 18 pmol/min per mg protein).
[c]Activity was measured in HaCaT cell extracts with 100 µM [$^3$H]NArPE as substrate (control = 12 + 3 pmol/min per mg protein).
[d]Binding was measured in mouse brain membrane fractions with 400 pM [$^3$H]CP55.940 as ligand (control = 82 ± 8 fmol/mg protein).
[e]Binding was measured in mouse spleen membrane fractions with 400 pM [$^3$H]CP55.940 as ligand (control = 58 ± 4 fmol/mg protein).
[f]Binding was measured in C6 cells membrane fractions with 500 pM [$^3$H]RTX as ligand (control = 141 ± 22 fmol/mg protein).
Data are means ± S.D. of three independent experiments.

Fluorescence Microscopy of b-AEA Transport

In order to ascertain whether b-AEA can be used as a probe to visualize the internalization of AEA by intact cells, we next performed conventional fluorescence microscopy in human HaCaT keratinocytes. Biotin-AEA (5 M per test) was detected by indirect immunofluorescence, using an anti-biotin monoclonal antibody and an anti-mouse secondary antibody conjugated with a green-fluorescent dye. The immunostaining revealed that cells quickly take up b-AEA, which appears to accumulate both in the cytosol and in the nucleus (FIG. 3, b-AEA). This transport was not attributable to the biotin moiety of the probe, since the biotin reagent per se was not taken up by the cells under the same experimental conditions (FIG. 3, biotin). In addition, we tested the specificity of b-AEA immunostaining in the presence of 5 µM OMDM-1, a selective inhibitor of AMT, or of 1 µM URB597, a selective inhibitor of FAAH. A remarkable decrease of immunostaining was observed only in HaCaT cells pretreated with OMDM-1, strongly indicating that b-AEA was indeed taken up by a true AMT-dependent process (FIG. 3, b-AEA/OMDM1). Instead, the inhibition of FAAH activity did not affect the uptake and intracellular trafficking of b-AEA (FIG. 3, b-AEA/URB597). Finally, neither 10 µM SR141716 nor 10 µM SR144528, selective antagonists of CB1R or CB2R respectively, nor 10 µM capsazepine, a selective antagonist of TRPV1 [Bari et al., 2006], affected the immunostaining of HaCaT cells with b-AEA (data not shown).

Effect of b-AEA on Keratinocyte Differentiation

Treatment of HaCaT cells with TPA plus calcium led to a ~400% increase in cornified envelope (CE) formation (FIG. 4), a hallmark of keratinocyte differentiation [Maccarrone et al., 2003]. Recently we have shown that administration of AEA to HaCaT cells dose-dependently reduces CE formation, reaching a maximum effect at 1 µM [Maccarrone et al., 2003]. We also showed that this activity of AEA was mediated by CB1R, and in fact it was fully reversed by 0.1 µM SR141716, but not by 0.1 µM SR144528 [Maccarrone et al., 2003]. Here, we confirmed that HaCaT cell differentiation is blocked by exogenous AEA in a CB1R-dependent manner, and supplement that b-AEA is instead ineffective under the same conditions (FIG. 4). These functional data are in keeping with the observation that [$^3$H]b-AEA does not bind to CB1 receptors of HaCaT cells (FIG. 2C), with the lack of interference of this biotin-derivative with the binding of [$^3$H] CP55.940 to an authentic CB1R (Table 2), and with the lack of effect of SR141716 on b-AEA immunostaining of HaCaT cells (not shown).

The invention will be further described in all details by the following examples which however are not intended to limit the scope of the conferred protection.

EXAMPLES

Example 1

Synthesis of (+)-N-arachidonoyl-biotinyl-3,6-dioxaoctanediamine (Biotin-AEA)

A biotin-derivative of N-arachidonoylethanolamine, was prepared using the biotinylation reagent EZ-Link Biotin-PEO-Amine (PIERCE, Rockford, Ill.). O-(7-azabenzotriazol-1-yl)-N,N,N',N'-tetramethyluronium-hexafluorophosphate (HATU; 16.3 mg, 1.3 eq; Sigma Chemical Co.; St. Louis, Mo.) and N,N-diisopropylethylamine (DIPEA; 0.017 mL, 3 eq; Sigma Chemical Co.; St. Louis, Mo.) were added to a solution of arachidonic acid (AA; 0.010 g; Sigma Chemical Co.; St. Louis, Mo.) in dimethylformamide (1 mL; Sigma Chemical Co.; St. Louis, Mo.). After stirring for 1 h, the biotinylation reagent (0.012 g, 1 eq; PIERCE, Rockford, Ill.) was added, and the resulting mixture was stirred at room temperature for 24 h. The solution was diluted with ethyl acetate and water, and the organic phases were washed sequentially with 1N HCl solution, NaHCO$_3$ saturated solution and brine; then, they were dried, concentrated under reduced pressure and purified on silica gel (0-15% methanol in chloroform). The synthesis of the radiolabelled [$^3$H]b-AEA was carried out under the same experimental conditions, by using a mix of arachidonic acid (AA) and [$^3$H]AA (Perkin-Elmer Life Sciences, Inc.; Boston, Mass.) (specific activity 10 mCi/mmol). The synthetic route allowed to produce the cold biotinylated-derivative of AEA (biotin-AEA, b-AEA or MM22) with a yield of ~50%. The identity and purity of this compound was checked by HPLC-ESI-MS and $^1$H NMR. Biotin-AEA showed an ESI-MS spectrum with m/z 661.8 [M+H]$^+$ (FIG. 1B), and a $^1$H NMR (FIG. 1C), (CD3CN) spectrum showing δ: 0.88 (3H, t, J=5.1 Hz), 1.24-1.47 (6H, m), 1.49-1.74 (8H, m), 2.06-2.31 (8H, m, partially under water residual peak), 2.66 (1H, d, J=12.9 Hz), 2.77-2.96 (7H, m), 3.14-3.23 (1H, m), 3.26-3.36 (4H, m), 3.46-3.55 (4H, m), 3.58 (4H, s), 4.18-4.29 (1H, m), 4.40-4.46 (1H, m), 5.26-5.48 (8H, m), 6.51-6.56 (bs, 2H). HPLC-ESI-MS and $^1$H NMR were performed by Waters apparatus and Bruker AM series spectrometers at 300 K and 300 MHz, respectively.

Example 2

AMT Assay in HaCaT Cells

HaCaT cells [Maccarrone et al., 2003], were cultured in Dulbecco's minimal essential supplemented with 10% fetal calf serum and 100 units/mL streptomycin/penicillin at 37° C. in a 5% CO$_2$ humidified atmosphere. Cells were split twice a week at 1:5 ratio using 0.05% trypsin (w/v), 0.02% EDTA (w/v) in phosphate-buffered saline (PBS). These cells were grown in six-well plates (2×10$^6$ cells/well) and were incubated for 10 min at 37° C. with [$^3$H]AEA (Perkin-Elmer Life Sciences, Inc.; Boston, Mass.) or [$^3$H]b-AEA, and were washed three times with cold PBS containing 1% bovine serum albumin. To discriminate noncarrier-mediated from carrier-mediated transport of AEA, control experiments were carried out at 4° C. and the values subtracted from those at 37° C. Then, the cells were solubilized in 1 ml of 0.1 M NaOH and neutralized (50 µl of concentrated HCl), and radioactivity was determined by liquid scintillation counting. Incubations were also carried out with different concentrations of [$^3$H]AEA or [$^3$H]b-AEA, as indicated in the figures, to determine the apparent Michaelis-Menten constant ($K_m$) and maximum velocity ($V_{max}$). The effect of different compounds on AEA or b-AEA uptake was determined by adding each substance directly to the incubation medium, at different concentrations. The results are shown in FIG. 2A, Table 1 and Table 2.

Example 3

FAAH Activity

The assay of fatty acid amide hydrolase (E.C. 3.5.1.4, arachidonoylethanolamide amidohydrolase; FAAH) was performed by measuring the release of [$^3$H]AA from [$^3$H]AEA (68 mCi/mmol) or [$^3$H]b-AEA (10 mCi/mmol) through reversed phase high performance liquid chromatography (RP-HPLC) and on-line scintillation counting. [$^3$H]AEA or [$^3$H]b-AEA was added to hydrolase assay buffer (50 mM Tris.HCl, pH 9.0) at the indicated concentrations. The reaction was initiated by the addition of HaCaT cell extracts, was continued at 37° C. for 15 min, and then was stopped by the addition of methanol/chloroform/water, with vortexing. This mixture was centrifuged at 3000×g for 5 min, the lower organic phase was dried and the pellet was resuspended in 20 µl of methanol and subjected to RP-HPLC analysis for AA quantitation. The separations of [$^3$H]AEA or [$^3$H]b-AEA from [$^3$H]AA were carried out on a C18 (5 µm, 3.0×150 mm) column, with a mobile phase of methanol-water-acetic acid (85:15:0.1, v/v/v), at a flow rate of 0.8 ml/min. The amount [$^3$H]AA formed were calculated from the corresponding peak areas. The effect of different concentrations of b-AEA on [$^3$H]AEA hydrolysis was ascertained by adding the "cold" compound directly to the assay buffer. FAAH activity was expressed as pmol [$^3$H]AA released from [$^3$H]AEA per min per mg protein. The results are shown in FIG. 2B, Table 1 and Table 2.

Example 4

Receptor Binding Assays

Figure 2C:
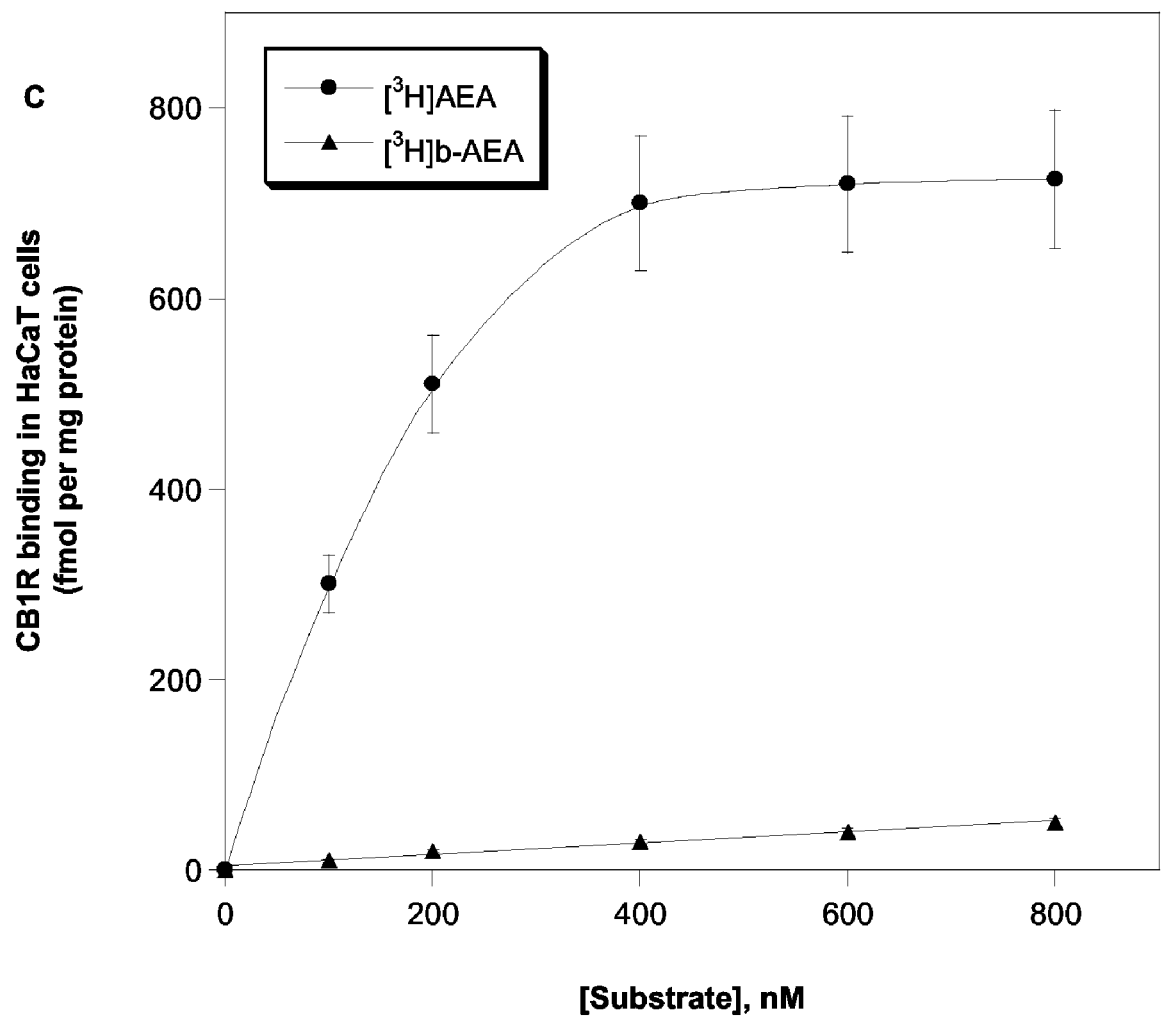

For cannabinoid receptor studies, HaCaT cells, mouse brain or mouse spleen were homogenized in 2 mM Tris-EDTA, 320 mM sucrose, 5 mM $MgCl_2$, 100 µM PMSF buffer (pH 7.4), using a Potter homogenizer, and were centrifuged three time at 1000×g (10 min), discharging the pellet. The supernatant was centrifuged at 18000×g (30 min), and the pellet was resuspended in assay buffer (50 mM Tris-HCl, 2 mM Tris-EDTA, 3 mM $MgCl_2$, 100 µM PMSF, pH 7.4), to a final protein concentration of 1 mg/ml. These membrane fractions were used in rapid filtration assays with [$^3$H]AEA, [$^3$H]b-AEA, or [$^3$H]CP55.940 (Perkin-Elmer Life Sciences, Inc.; Boston, Mass.). For vanilloid receptor studies, that are not expressed by HaCaT cells, membrane fractions isolated from rat neuroblastoma C6 cells were used in rapid filtration assays with [$^3$H]RTX (Perkin-Elmer Life Sciences, Inc.; Boston, Mass.). The effect of different compounds on CBR or TRPV1 binding was tested. Binding data from HaCaT cell membranes were elaborated through nonlinear regression analysis, using the Prism 4 program (GraphPAD Software for Science), in order to calculate apparent dissociation constant (Kd) and maximum binding (Bmax) of [$^3$H]AEA or [$^3$H]b-AEA. The results are shown in FIG. 2C, Table 1 and Table 2.

Example 5

NAPE-PLD Activity

HaCaT cell extracts (100 µg/test) were incubated at 37° C. for 30 min with a clear mixture of [$^3$H]NArPE (ARC; St. Louis, Mo.) and NArPE ("cold" NArPE was synthesized from AA and phosphatidylethanolamine) at a final specific activity of 6.8 nCi/nmol, in 200 µl of 50 mM Tris-HCl, pH 7.4, containing 0.1% Triton X-100. A mixture of chloroform/methanol (2:1, v/v; 600 µl) was added to stop the reaction. Then, the samples were vortexed and centrifuged at room temperature, and the lower organic phase was dried. The pellet was resuspended in 20 µl of methanol and subjected to RP-HPLC coupled to on-line scintillation counting. The separations were carried out on a C18 (5 µm, 3.0×150 mm) column with a mobile phase of methanol-water-acetic acid (85:15:0.1, v/v/v), at a flow rate of 0.8 ml/min. The amount of [$^3$H]AEA formed was calculated from the corresponding peak areas. The identity of the peaks was assessed also by UV detection of cold standard, recording absorbance at 204 nm. The effect of b-AEA on NAPE-PLD activity was ascertained by adding different concentrations of the biotin-derivative directly to the assay buffer. NAPE-PLD activity was expressed as pmol [$^3$H]AEA released from [$^3$H]NArPE per min per mg protein. The results are reported in Table 2.

Example 6

Fluorescence Microscopy Studies in HaCaT Cells

HaCaT cells were plated at a density of 6×10$^4$ cells/ml on collagen-coated (0.5 mg/ml; Sigma, St. Louis, Mo.) glass coverslips (12 mm). Twenty-four hours after plating, cultures were either left untreated (by adding 5 M biotin EZ-Link Biotin-PEO-Amine, as negative control) or incubated with 5 M b-AEA for 10 min at 37° C. in a 5% $CO_2$ humidified atmosphere. The effects of 1 µM URB597 (Cayman Chemicals; Ann Arbor, Mich.), a selective inhibitor of the AEA hydrolase FAAH, of 5 µM OMDM-1, a selective inhibitor of the AEA transporter AMT, of 10 µM SR141716 or 10 M SR144528, selective antagonists of CB1R and CB2R respectively, or of 10 µM capsazepine (Calbiochem; La Jolla, Calif.), a selective antagonist of TRPV1, on the uptake of b-AEA were determined by adding each substance directly to the incubation medium, 5 min before probe addition. All steps of the immunofluorescence procedure were performed at room temperature. Cells were washed, fixed with 3% paraformaldehyde (Sigma) for 20 min, and then permeabilized with 0.1% Triton X-100 in PBS for 15 min. After a blocking step in Image-iT™ FX signal enhancer (Molecular Probes, Eugene, Oreg.) for 30 min, cells were incubated for 1 h with anti-biotin primary antibody (Molecular Probes, Eugene, Oreg.), diluted 1:50 in Image-iT™ FX signal enhancer. After three washes with PBS (10 min each one), anti-mouse secondary antibody conjugated to Alexa Fluor 488 (Molecular Probes, Eugene, Oreg.) were diluted 1:100 in Image-iT™ FX signal enhancer and incubated with the specimens for 30 min. After washing steps as above, the coverslips were mounted using the antifade prolong Gold reagent (Molecular Probes, Eugene, Oreg.) and visualized by Nikon Eclipse E800 fluorescence microscopy, equipped with a filter pack for the green fluorescence detection (ex 465-495/em 515-555) (Nikon Instruments, Tokyo, Japan). N-Piperidino-5-(4-chlorophenyl)-1-(2,4-dichloro-phenyl)-4-methyl-3-pyrazole carboxamide (SR141716), and N-[1(S)-endo-1,3,3-trimethyl-bicyclo[2.2.1]heptan-2-yl]-5-(4-chloro-3-methylphenyl)-1-(4-methyl-benzyl)-pyrazole-3-carboxamide (SR144528) were kind gifts from Sanofi-Aventis Recherche (Montpellier, France). OMDM-1 was a kind gift from Dr. S. Marinelli (Experimental Neurology, IRCCS Fondazione Santa Lucia, Rome, Italy). The results are shown in FIG. 3.

Example 7

Evaluation of HaCaT Cell Differentiation

Cell differentiation was induced by treating HaCaT cells with 12-O-tetradecanoylphorbol 13-acetate (TPA; 10 ng/ml) plus calcium chloride ($CaCl_2$; 1.2 mM) for 5 days, as reported [Maccarrone et al., 2003]. AEA and b-AEA (or vehicle in the controls) were added directly to the culture medium at the same time as TPA plus calcium. Cornified envelope (CE), a hallmark of keratinocyte differentiation, was extracted from HaCaT cells (5×10$^6$/test) by exhaustive boiling and sonication in 2% SDS, 20 mM dithiothreitol, 0.1 M Tris-HCl pH 8.0, and 0.5 mM EDTA. CEs were then purified on Ficoll gradients and recovered as sonicated fragments, free of soluble keratin/filaggrin proteins, after pelleting through Ficoll as previously described [Maccarrone et al., 2003]. CE formation was quantified by spectrophotometry at 600 nm and was normalized to the protein content. The results are shown in FIG. 4.

REFERENCES

Bari, M., Battista, N., Fezza, F., Gasperi, V., and Maccarrone, M. (2006) New insights into endocannabinoid degradation and its therapeutic potential. Mini-Rev. Med. Chem. 6, 109-120.

Battista, N., Gasperi, V., Fezza, F. and Maccarrone, M. (2005) The Anandamide Membrane Transporter and the Therapeutic Implications of its Inhibition. Therapy 2, 141-150.

Di Marzo, V., Bifulco, M. and De Petrocellis, L. (2004) The endocannabinoid system and its therapeutic exploitation. Nature Rev. Drug Discov. 3, 771-784.

Fezza, F., Gasperi, V., Mazzei, C. and Maccarrone, M. (2005) Radiochromatographic assay of N-acyl-phosphatidylethanolamine-specific phospholipase D (NAPE-PLD) activity. Anal. Biochem. 339, 113-120.

Howlett, A. C., Breivogel, C. S., Childers, S. R., Deadwyler, S. A., Hampson, R. E. and Porrino, L. J. (2004) Cannabinoid physiology and pharmacology: 30 years of progress. Neuropharmacol. 47, 345-358.

Maccarrone, M., Di Rienzo, M., Battista, N., Gasperi, V., Guerrieri, P., Rossi, A. and Finazzi-Agrò, A. (2003) The endocannabinoid system in human keratinocytes: evidence that anandamide inhibits epidermal differentiation through CB1 receptor-dependent inhibition of protein kinase C, activation protein-1, and transglutaminase. J. Biol. Chem. 278, 33896-33903.

Moore, S. A., Nomikos, G. G., Dickason-Chesterfield, A. K., Schober, D. A., Schaus, J. M., Ying, B. P., Xu, Y. C., Phebus, L., Simmons, R. M., Li, D., Iyengar, S, and Felder, C. C. (2005) Identification of a high-affinity binding site involved in the transport of endocannabinoids. Proc. Natl. Acad. Sci. USA 102, 17852-17857.

Muthian, S., Nithipatikom, K., Campbell, W. B. and Hillard, C. J. (2000) Synthesis and characterization of a fluorescent substrate for the N-arachidonoylethanolamine (anandamide) transmembrane carrier. J. Pharmacol. Exp. Ther. 293, 289-295.

Oddi, S., Bari, M., Battista, N., Barsacchi, D., Cozzani, I. and Maccarrone, M. (2005) Confocal microscopy and biochemical analysis reveal spatial and functional separation between anandamide uptake and hydrolysis in human keratinocytes. Cell. Mol. Life. Sci. 62, 386-395.

Pisani, A., Fezza, F., Galati, S., Battista, N., Napolitano, S., Finazzi-Agrò, A., Bernardi, G., Brusa, L., Pierantozzi, M., Stanzione, P. and Maccarrone, M. (2005) High endogenous cannabinoid levels in the cerebrospinal fluid of untreated Parkinson's disease patients. Ann. Neurol. 57, 777-779.

The invention claimed is:

1. A biotinyl-N-acyl-ethanolamine compound having formula I

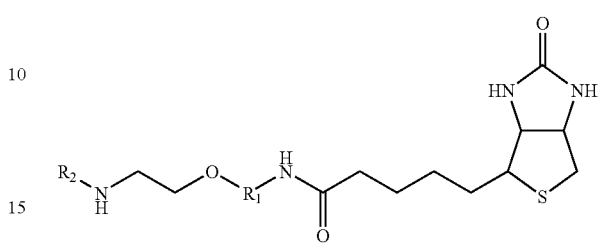

Formula I wherein $R_1$ is the spacer arm $R_{1A}$ or $R_{1B}$:

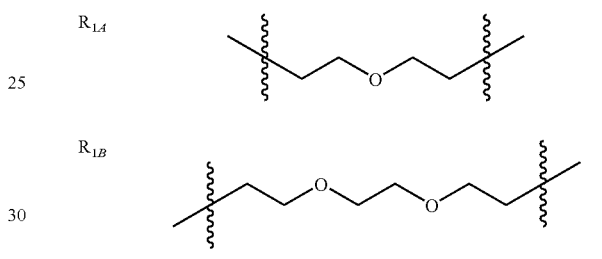

and $R_2$ is a saturated or unsaturated fatty acid residue selected from the group consisting of:

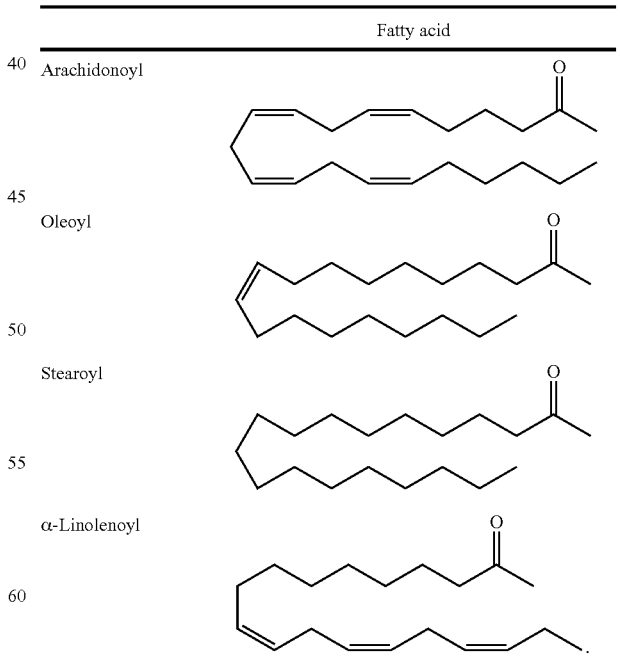

2. The biotinyl-N-acyl-ethanolamine compound according to claim 1, characterized in that the fatty acid residue is arachidonic acid.

3. An analytical reagent comprising a biotinyl-N-acyl-ethanolamine compound according to claim 1 as a probe for visualizing the internalization and trafficking of N-acyl-ethanolamine in intact cells.

4. A kit of reagents for use in an analytical method comprising a reagent according to claim 3 and a biotin-affinity partner capable of being detected.

5. The kit of reagents according to claim 4, wherein the biotin-affinity partner is a labeled avidin or a labeled anti-biotin antibody.

6. The kit according to claim 5, wherein the biotin-affinity partner is labeled with a detectable moiety selected from the group consisting of: fluorophores, fluorescent microspheres, enzymes, chromophores, magnetic particles and colloidal gold.

7. A method for visualizing the internalization and trafficking of AEA by intact cells, or for monitoring the cell AEA-transporter molecules, comprising contacting, sequentially or concomitantly, the cells with a reagent comprising a biotinyl-N-acyl-ethanolamine compound, then with a biotinyl-affinity partner capable of being detected and detecting the labeling moiety, wherein the biotinyl-N-acyl-ethanolamine compound has formula I

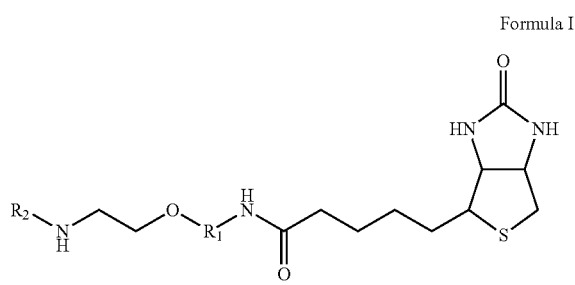

Formula I wherein $R_1$ is the spacer arm $R_{1A}$ or $R_{1B}$:

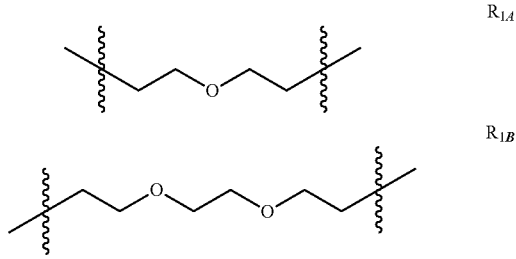

$R_{1A}$ $R_{1B}$ and $R_2$ is a saturated or unsaturated fatty acid residue selected from the group consisting of:

| Fatty acid group | |
|---|---|
| Arachidonoyl | 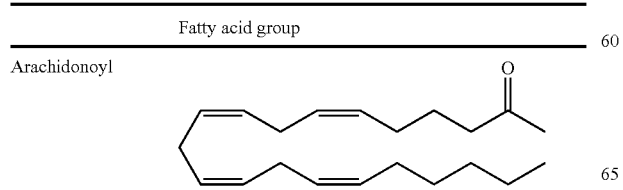 |
| Palmitoyl | 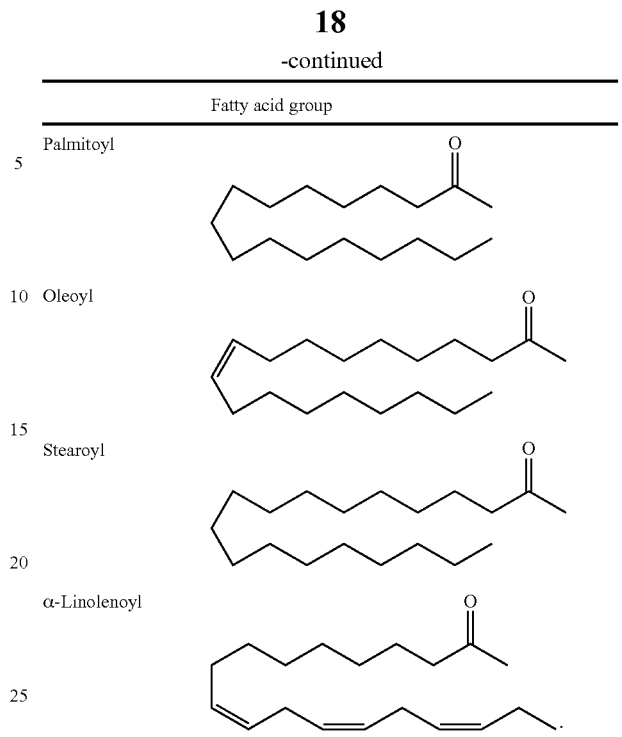 |
| Oleoyl | |
| Stearoyl | |
| α-Linolenoyl | |

8. A diagnostic reagent comprising a biotinyl-N-acyl-ethanolamine compound according to claim 1 as a probe for monitoring unpaired parameters in the endocannabinoid system or the level of circulating endogenous AEA.

9. The diagnostic reagent according to claim 8 for use in a diagnostic method for Parkinson's disease, schizophrenia, multiple sclerosis, obesity, risk of miscarriage, risk of cardiovascular diseases or risk of vascular dysfunctions.

10. A diagnostic kit comprising the diagnostic agent according to claim 8 and a biotin-affinity partner capable of being detected.

11. The diagnostic kit according to claim 10, wherein the biotin-affinity partner is labeled with a detectable moiety selected from the group consisting of: fluorophores, fluorescent microspheres, enzymes, chromophores, magnetic particles and colloidal gold.

12. An in vitro diagnostic method for monitoring unpaired parameters in the endocannabinoid system or the level of circulating endogenous AEA comprising contacting, in a competition assay, a sample to be diagnosed with a diagnostic agent comprising a biotinyl-N-acyl-ethanolamine compound, then with a biotinyl-affinity partner capable of being detected and detecting the labeling moiety, wherein the biotinyl-N-acyl-ethanolamine compound has formula I

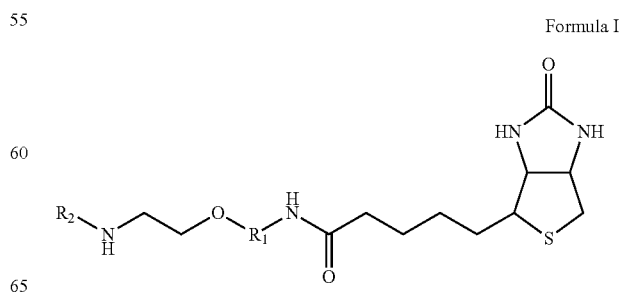

Formula I wherein $R_1$ is the spacer arm $R_{1A}$ or $R_{1B}$:

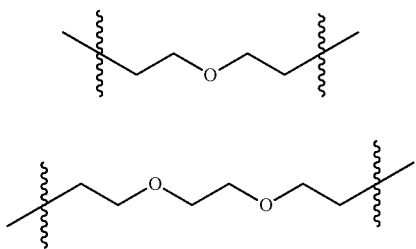

and $R_2$ is a saturated or unsaturated fatty acid residue selected from the group consisting of:

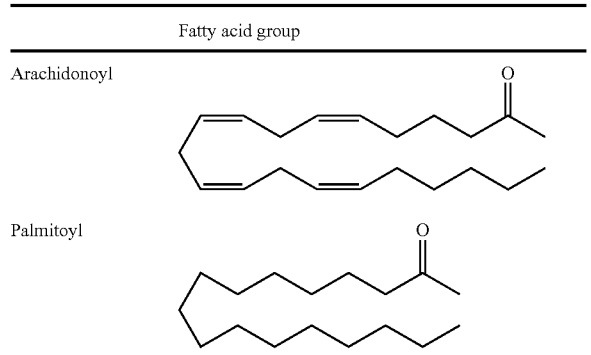

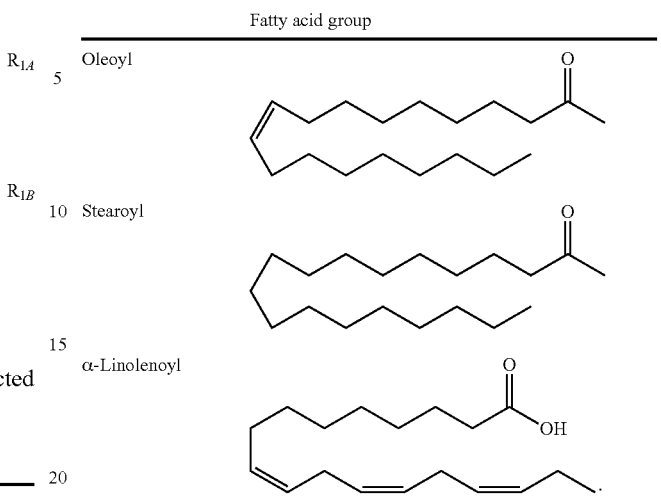

13. The diagnostic method according to claim 12 for the diagnosis of Parkinson's disease, schizophrenia, human multiple sclerosis, obesity, risk of miscarriage, risk of cardiovascular diseases or risk of vascular dysfunctions.

14. The diagnostic method according to claim 12, wherein the biotinyl-N-acyl-ethanolamine compound is biotinyl-N-arachidonoylethanolamine.

15. The diagnostic method according to claim 12, wherein the biotin-affinity partner is labeled with a detectable moiety selected from the group comprising: fluorophores, fluorescent microspheres, enzymes, chromophores, magnetic particles and colloidal gold.

* * * * *